United States Patent [19]

Peters

[11] Patent Number: 5,031,607
[45] Date of Patent: Jul. 16, 1991

[54] ANKLE BRACE

[75] Inventor: Rick E. Peters, Louisville, Ky.

[73] Assignee: Active Ankle Systems, Inc., Louisville, Ky.

[21] Appl. No.: 404,125

[22] Filed: Sep. 7, 1989

[51] Int. Cl.⁵ ............................................. A61F 5/00
[52] U.S. Cl. ................................ 128/80 H; 128/80 R; 2/22
[58] Field of Search ................ 128/80 R, 80 H, 83, 128/83.5, 84 R, 85, 87 R, 88; 2/22

[56] References Cited

U.S. PATENT DOCUMENTS

| Re. 15,446 | 9/1922 | Hamilton . | |
|---|---|---|---|
| 112,952 | 3/1871 | Niswander . | |
| 130,639 | 8/1872 | Howe | 128/88 |
| 297,368 | 8/1888 | Womack . | |
| 830,894 | 9/1906 | Garrod . | |
| 3,506,000 | 4/1970 | Baker . | |
| 3,674,023 | 7/1972 | Mann . | |
| 3,955,565 | 5/1976 | Johnson, Jr. . | |
| 4,133,311 | 1/1979 | Karczewski . | |
| 4,166,460 | 9/1979 | Applegate . | |
| 4,280,488 | 7/1981 | Polsky . | |
| 4,280,489 | 7/1981 | Johnson, Jr. . | |
| 4,287,920 | 9/1981 | Johnson, Jr. . | |
| 4,320,748 | 3/1982 | Racette . | |
| 4,378,793 | 4/1983 | Mauldin et al. | 128/80 H |
| 4,409,976 | 10/1983 | Pence | 128/80 H X |
| 4,433,682 | 2/1984 | Bodra | 128/80 R X |
| 4,510,927 | 4/1985 | Peters . | |
| 4,556,054 | 12/1985 | Paulseth | 128/80 H |
| 4,577,419 | 3/1986 | Chassaing | 128/80 H X |
| 4,587,962 | 5/1986 | Greene . | |
| 4,590,932 | 5/1986 | Wilkerson | 128/80 H X |
| 4,628,945 | 12/1986 | Johnson, Jr. | 128/80 H |
| 4,665,904 | 5/1987 | Lerman | 128/80 H |
| 4,693,239 | 9/1987 | Clover, Jr. | 128/88 X |
| 4,844,094 | 7/1989 | Grim | 128/80 H |
| 4,865,023 | 9/1989 | Craythorne et al. | 128/80 H |

Primary Examiner—Richard J. Apley
Assistant Examiner—Linda C. M. Dvorak
Attorney, Agent, or Firm—Middleton & Reutlinger

[57] ABSTRACT

An ankle brace for protecting and exercising an injured ankle includes a heel portion, inner and outer pivot legs, and padding which lies between the wearer's leg and the brace.

12 Claims, 5 Drawing Sheets

ANKLE BRACE

BACKGROUND OF THE INVENTION

The present invention relates to ankle braces, and, in particular, to an ankle brace which permits flexing of the ankle forward and backward (plantarflexion and dorsiflexion) while preventing the ankle from flexing inward or outward (inversion or eversion), in order to promote healing of an injured ankle or prevent injury to an injury-prone ankle during exercise.

Ankle injuries are among the most common injuries in sports. In order to protect the ankle, many athletes have wrapped the ankle area with adhesive tape. The application of tape is expensive both because it is time consuming and because of the cost of the tape itself. It is also not very effective, because the tape loosens quickly after exercise is begun. The use of tape has also been shown to weaken ankles if used over a long period of time because it causes a loss of plantarflexion and dorsiflexion.

When an ankle is injured, the traditional method for promoting healing is to apply pressure to the area to reduce swelling. The current method for applying pressure is to apply it over a large area, which limits the range of motion of the ankle. When large areas are covered by a compression device, the material contacting the foot must be fairly flexible or soft, such as an elastic bandage or an air bag, in order to avoid being uncomfortable. This severely limits the amount of pressure that can be applied to the injury site to reduce swelling. Also, with an air bag, the foot rubs against the bag in order to move, causing irritation to the foot, and generating heat. It is not desirable to add heat to a swollen ankle.

Another treatment method is to exercise the joint to promote healing. Exercise brings greater blood flow to the area and prevents the atrophy of muscles. The current trend in medicine is to promote exercise as soon as possible. However, in traditional treatment methods, the ankle could not be properly exercised until after the compression was removed, thereby greatly delaying the exercise therapy.

SUMMARY OF THE INVENTION

The present invention provides a reusable ankle brace which closely conforms anatomically to the ankle so that it is comfortable and so that it pivots along the same axis as the ankle.

The present invention provides the greatest possible flexing of the ankle forward and backward (plantarflexion and dorsiflexion) while preventing inversion and eversion of the ankle in order to promote healing.

In addition, the present invention provides an ankle brace with interchangeable pads, so that a thick and relatively stiff compression pad can be used to provide uniform pressure directly on the injured area shortly after it is injured, and, when the swelling is reduced, a thinner exercise pad can be inserted to permit greater freedom of movement.

The compression pad of the present invention covers much less of the foot than other devices, concentrating its compressive force in the area of the injury and leaving the rest of the foot free to move. This means that there is more freedom of movement in plantarflexion and dorsiflexion with the present invention. Plantarflexion and dorsiflexion do not usually cause injury, so this kind of motion is desirable in order to promote healing and reduce muscle atrophy.

The fact that the compression pad of the present invention concentrates its compressive force in the area of the injury also means that this compression pad can be relatively rigid and therefore apply more pressure to the injured area without being uncomfortable.

The use of the ankle brace of the present invention provides the optimum combination of pressure applied to the injured area to reduce swelling and flexibility of the joint to permit exercise which promotes healing and reduces muscle atrophy. In this way, a single brace provides the benefits both of a compression strategy and an exercise strategy to promote healing, while protecting the ankle from further injury.

The ankle brace of the present invention also gives the wearer control over the treatment of the injury, which permits the treatment to be quickly changed, depending on the condition of the ankle.

In addition, the present invention provides a rear, angular strap which improves the function of the brace. It eliminates any problem with the brace sliding forward on the foot while, at the same time, providing a better fit and providing an additional force to prevent inversion. Since inversion injuries are about 85% of the ankle injuries, this additional support is very helpful.

In one embodiment, the invention includes a cold pack insert, which can be used shortly after injury to reduce swelling. The cold pack may also be used periodically as needed, such as to prevent swelling after exercise.

In addition, the present ankle brace is designed so that it provides the same excellent fit on either the left or right foot, thereby reducing the number of braces that need to be kept in stock in a doctor's or trainer's office while overcoming the problems of box-like, symmetrical braces which do not provide good fit.

DESCRIPTION OF THE PREFERRED EMBODIMENTS

The present invention is an ankle brace 2 which includes a heel stirrup 4, to which are attached an inner pivot leg 6, an outer pivot leg 8, and a pivot strap 10.

Rivets 12 and 14 connect the inner pivot leg 6 and outer pivot leg 8, respectively, to the heel stirrup 4. The outer rivet 14 preferably is positioned slightly lower than the inner rivet 12 to correspond with the outer and inner pivot points of the ankle bones (the lateral malleolus and medial malleolus, respectively). This can be seen most clearly in FIG. 4, in which the distance "a" from the outer rivet 14 to the flat bottom 30 of the heel stirrup 4 is less than the distance "b" from the inner rivet 12 to the flat bottom 30. Thus, the ankle brace pivots along the same axis as the foot, providing maximum comfort and maximum flexing of the ankle forward and backward (plantarflexion and dorsiflexion). The heel stirrup 4 and the pivot legs 6, 8 are made of a relatively stiff material, such as polypropylene, and they overlap substantially in the vertical direction, so as to severely limit flexing inward or outward (inversion or eversion). Inward and outward flexing could reinjure the ankle and therefore must be prevented while still permitting as much flexibility of the ankle as possible.

Figures 1, 2:
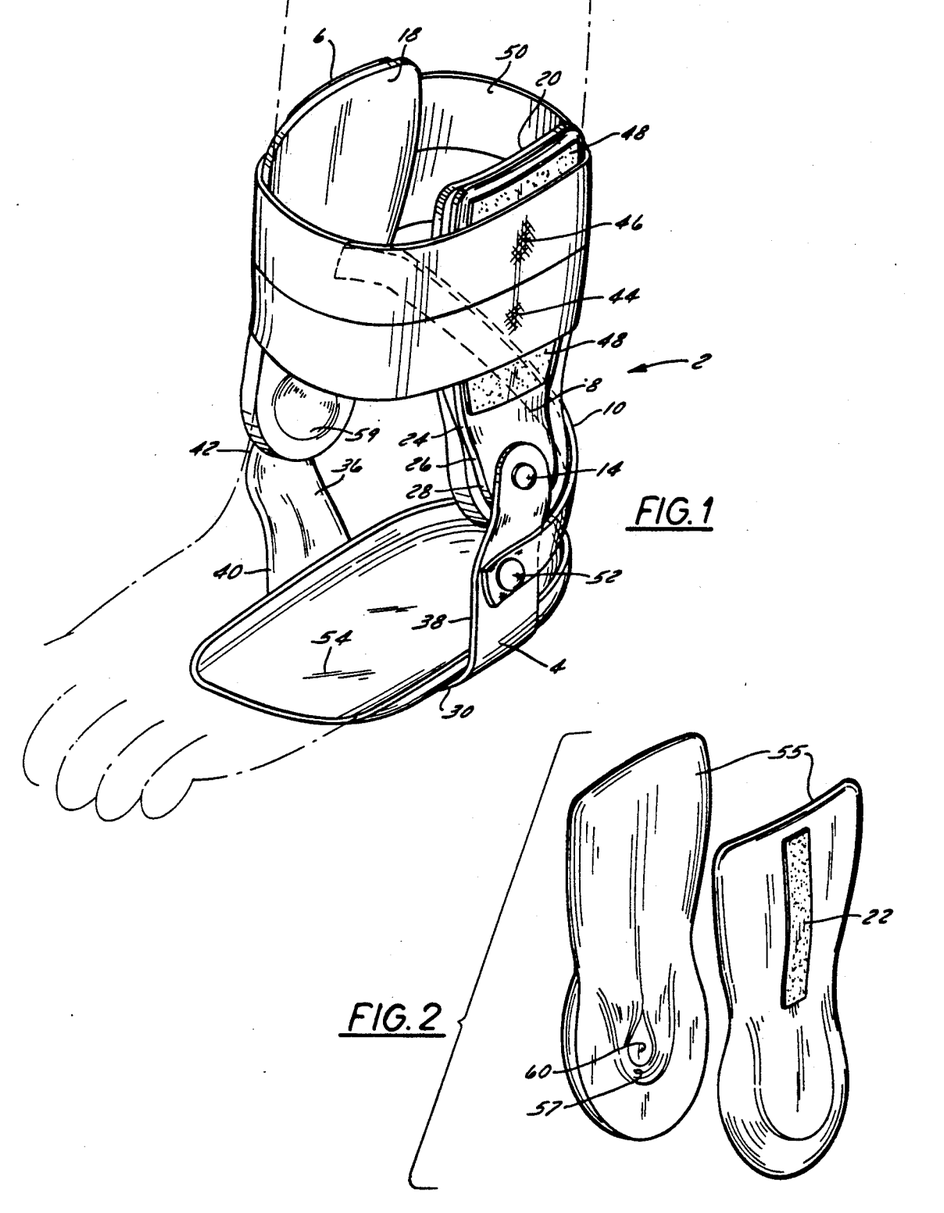
FIG. 1 is a perspective view taken from the front left side of an ankle brace made in accordance with the present invention, including two exercise pads, and showing the left foot.
FIG. 2 is a perspective view of two compression pads made in accordance with the present invention.
Figure 3:
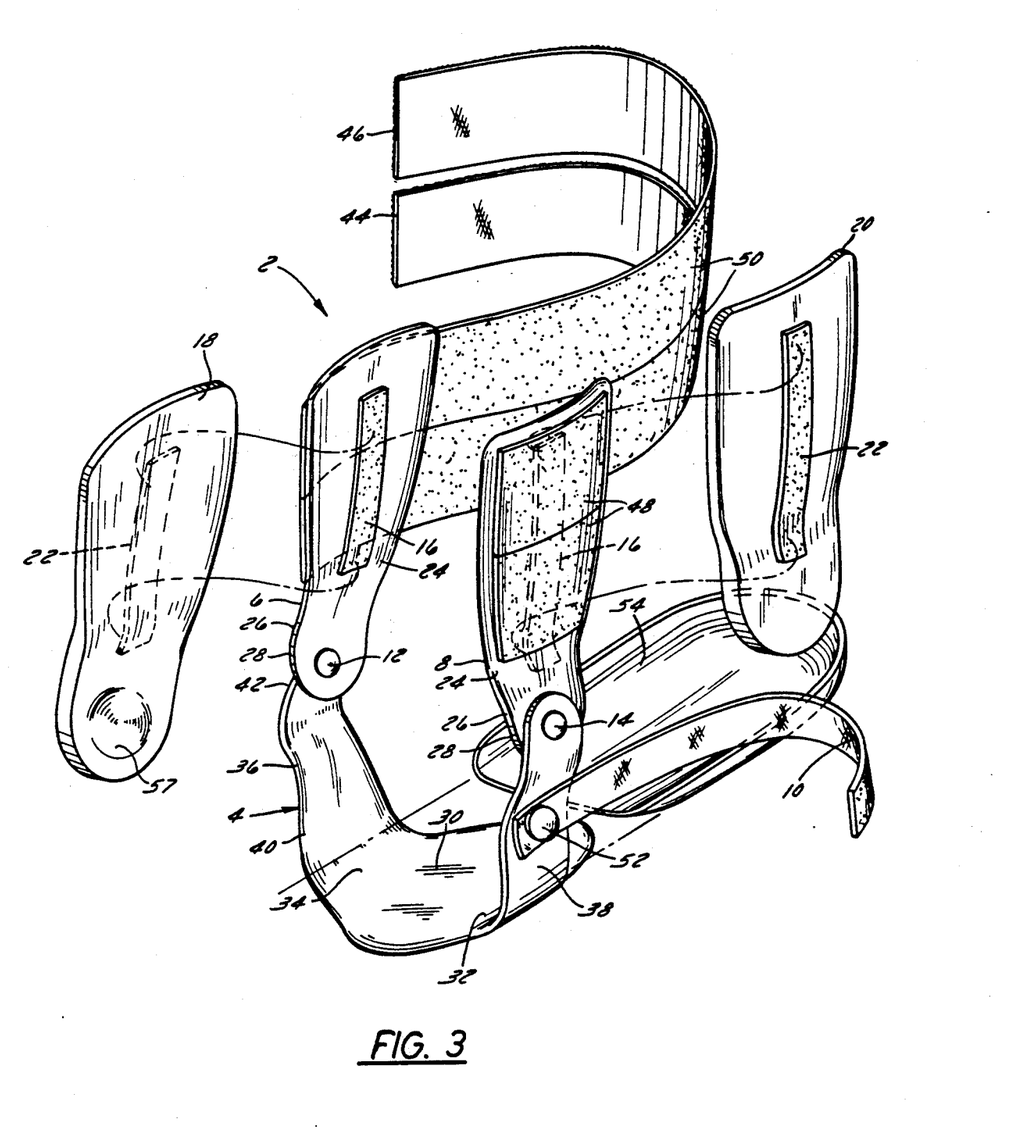
FIG. 3 is an exploded perspective view of the ankle brace of FIG. 1.
Figures 4, 5, 6:
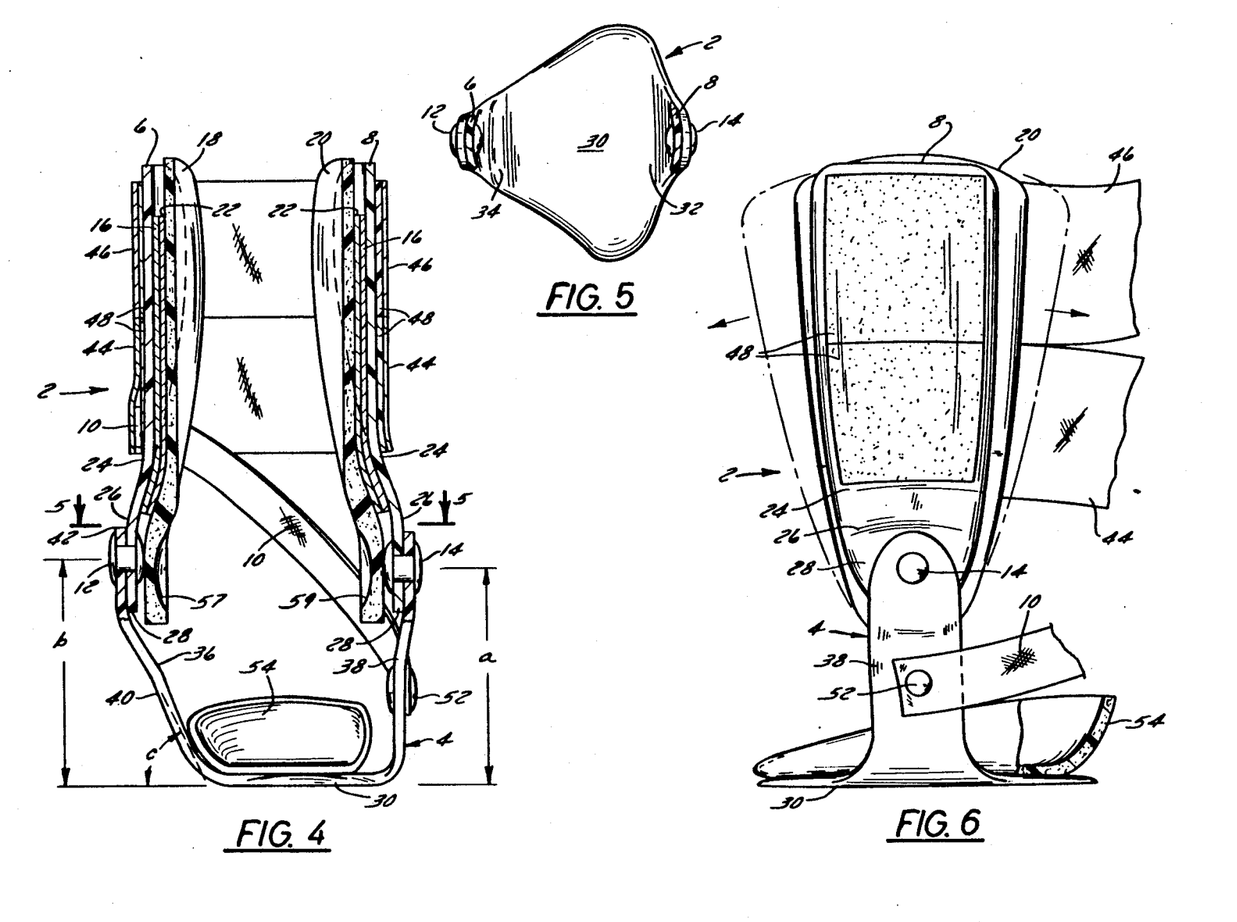
FIG. 4 is a front view of the ankle brace of FIG. 1.
FIG. 5 is a view taken along the section 5—5 of FIG. 4, with the heel pad removed.
FIG. 6 is a side view of the ankle brace of FIG. 4, with different positions shown in phantom.

On the inside of the pivot legs 6, 8 are releasable attachment means 16. In this embodiment, strips of material including the hook side of a hook and loop type of connector such as the Velcro TM brand are glued to the pivot legs at the points 16. As shown in FIGS. 1, 3 and 4, inner and outer exercise pads 18, 20 are mounted on the inside of the inner and outer pivot legs 6, 8, respectively. Each exercise pad 18, 20 has a strip of loop connector material 22 glued to its outer surface. This strip 22 mates with the corresponding strip 16 on the inside of the pivot legs 6, 8. This permits the pads 18, 20 to be easily attached to and removed from the ankle brace 2. This method of attachment also permits the pads 18, 20 to be adjusted up, down, forward, or rearward to fit the wearer.

The inner and outer pivot legs 6, 8 are contoured at the top to wrap partway around the side of the wearer's leg. This contour provides good surface area contact between the brace and the wearer's leg, which makes the brace comfortable and effective. The contour also prevents the pivot legs 6, 8 from sliding forward or backward on the wearer's leg. The contour also permits a comfortable fit for a variety of sizes of wearers' legs.

The lower one-third of each of the pivot legs 6, 8 bends outward in the area 24 and then downward in the area 26. This imitates the shape of the inner and outer ankle bones, thereby providing maximum surface area contact in the area of the ankle which needs support. This makes the brace more comfortable and more effective than if the pivot legs 6, 8 were straight. It also makes the brace smaller so it can fit into the wearer's shoe more readily. The lowermost portion 28 of the pivot legs (through which the rivets 12, 14 pass) lies in a vertical plane (perpendicular to the flat bottom 30 of the heel stirrup 4) to encourage the forward and backward flexing of the foot while restricting inward and outward flexing.

The heel stirrup 4 fits inside the wearer's shoe, and the bottom 30 lies under the wearer's heel. As shown in FIG. 5, the flat bottom 30 is considerably longer in the region 32 which lies below the outer pivot leg 8 than in the region 34, which lies below the inner pivot leg 6. The long area 32 provides a large support base for the outer portion of the foot, and the tapering of the bottom 30 to the shorter region 34 provides greater comfort in the arch area of the foot. While the brace is not symmetrical, it can be turned around and used on the other foot to provide the same excellent fit on either foot. This greatly reduces the inventory that a trainer or doctor would have to maintain.

The heel stirrup 4 is substantially U-shaped, with the flat bottom 30 connecting inner and outer upright portions 36, 38, respectively. The outer upright 38 extends substantially vertically from the flat bottom 30 for approximately one-third of its height, then bends outward slightly, and then returns to a substantially vertical direction in the portion through which the rivet 14 passes.

The inner upright 36 extends away from the base 30 at an angle C (shown in FIG. 4) of approximately seventy-five degrees. This angled portion 40 extends for approximately two-thirds of the height of the inner upright 36. This angle corresponds anatomically with the shape of the inside of the ankle when it is bearing weight. When the foot bears weight, the inside of the foot flattens and rolls slightly inward. The upper one-third portion 42 of the inner upright 36 extends vertically, putting it in line with the ankle bone. As was explained earlier, the outside rivet 14 defines a pivot point which is lower than the pivot point defined by the inside rivet 12. In other words, the outside pivot point 14 is located a shorter vertical distance from the flat bottom 30 of the stirrup than is the inside pivot point 12.

Two connecting straps 44, 46 are attached to the upper portion of the pivot legs 6, 8 to keep the pivot legs 6, 8 close to the user's leg. These straps 44, 46 preferably have a loop connector material on their inside surface 50, and the mating hook connector material is located in strips 48 glued to the outside of the pivot legs 6, 8. The outside surface of the straps 44, 46 may also include some of the hook connector material so that the straps 44, 46 can be securely wrapped onto themselves.

The pivot strap 10 is pivotably mounted on the lower straight portion of the outer upright 38 by means of a rivet 52. This means that the pivot strap 10 is riveted below the point at which the outer pivot leg 8 pivots relative to the stirrup 4. The pivot strap 10 crosses behind the wearer's leg and attaches to the hook connector strip 48 o the outside of the inner pivot leg 6. In this way, the strap 10 prevents the brace 2 from sliding forward relative to the user's foot. The angle of the strap 10 also provides force in the proper direction to hold the outer upright 38 close to the ankle and to prevent any increase in the angle between the inner upright 36 and the flat bottom 30 (which would be a decrease in the angle C of FIG. 4), thereby providing a force which opposes any inversion of the ankle. When the ankle brace 2 is turned around and used on the right foot (not shown), the pivot strap 18 simply pivots so that it will cross the other side of the brace (formerly the front side, which will then be the back).

A heel pad 54 may be placed on top of the flat bottom 30 to receive the wearer's heel. The heel pad 54 is preferably made of a soft urethane material which will cushion the wearer's heel. The heel pad 54 also cups the wearer's foot, surrounding the sides and back of the heel, which will reduce talar tilt, allowing for a quicker recovery from an injury.

Figure 7:
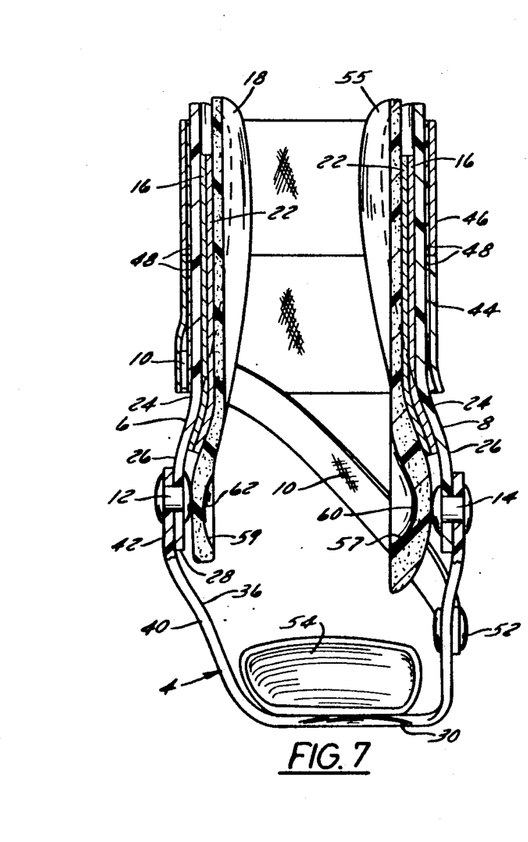
FIG. 7 is a front view of the ankle brace of FIG. 1 except that the outer exercise pad has been replaced by one of the compression pads shown in FIG. 2.
Figure 11:
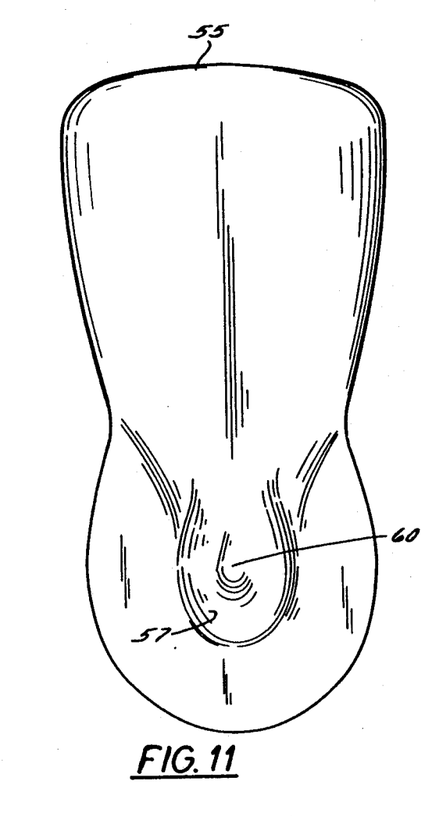
FIG. 11 is a side view showing the inside of the compression pad shown in FIG. 2.

A compression pad 55, as shown in FIGS. 2, 7, and 11 can be used to replace the exercise pad 18 or 20, when edema or swelling are present. The compression pad 55 will usually be worn only on the side of the foot that is injured, usually the outside, as shown in FIG. 7, leaving an exercise pad 20 or 18 on the other side. The compression pad 55 is made of a stiffer material than the exercise pad. In the preferred embodiment, both the exercise pads and the compression pads are made of urethane foam, and the compression pad is denser, making it stiffer. The compression pad is wider and thicker than the exercise pad in the area of the ankle and has a deep, rounded indentation 57 which cups around the ankle bone to provide localized pressure on the injury site.

As shown in FIG. 7, the deepest part 60 of the indentation 57 is aligned with the center of the rivet 14, which defines the pivot point. The exercise pad 18 also has an indentation 59 to receive the ankle bone, but that indentation 59 is much shallower than the indentation 57 of the compression pad 55. The deepest part 62 of the indentation 59 in the exercise pad 18 is also aligned with the pivot point of its respective side of the brace, but it should be noted that the compression pad extends a substantially greater distance downward from the deepest part 60 of its indentation 57 than does the exercise pad. This is necessary in order for the compression pad 55 to apply pressure completely around the bone on the side of the ankle that is injured. If the injury were on the inside of the ankle, the compression pad 55 and exercise pad 18 of FIG. 7 would switch sides, with each pad's indentation aligned with the pivot point of its respective side.

As with the exercise pads 18, 20, the compression pad 55 has a loop connector portion 22 on its outer surface which mates with the hook connector portion 16 on the inside of the pivot leg. This form of attachment permits the compression pad to be adjusted relative to the pivot leg 6 or 8 for the best fit. The compression pad 55 thereby fits precisely around the injured ankle to apply pressure directly on the injury. This permits greater pressure to be applied to the injury comfortably, without restricting movement any more than necessary. The compression provided by the compression pad 55 will reduce edema or swelling that may normally follow an injury or exercise. Reducing this swelling decreases the severity of the injury, shortens recovery time, decreases pain, and increases the range of motion of the joint.

The interchangeability of the exercise pad and the compression pad allows the wearer to control his own treatment, permitting him to use a compression pad when swelling is a problem and then to switch to the exercise pad as soon as the swelling goes down. This maximizes the benefits from both the compression and the exercise types of therapy. The compression pad 55 is curved or contoured in its upper two-thirds to help fit around the leg. This prevents the compression pad from sliding forward or backward on the user's leg.

Figure 8:
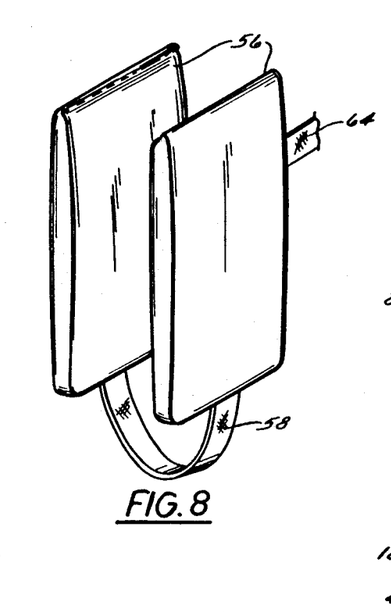
FIG. 8 is a perspective view of a pair of cold packs.
Figure 9:
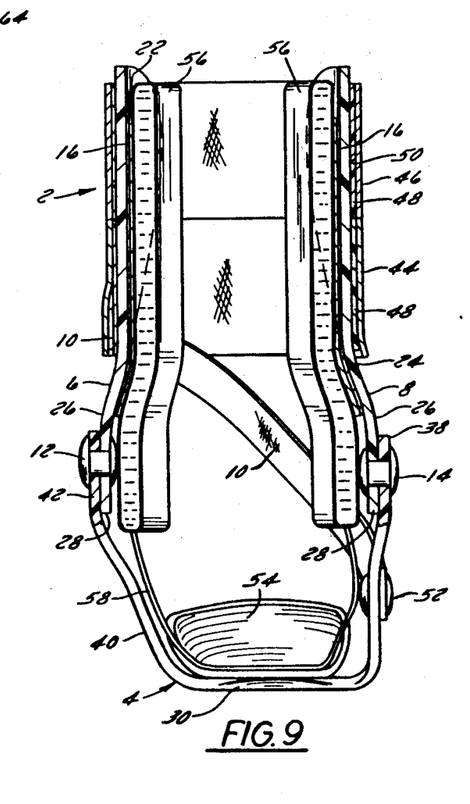
FIG. 9 is a front view of the device shown in FIG. 1 except that cold packs are replacing the exercise pads.
Figure 10:
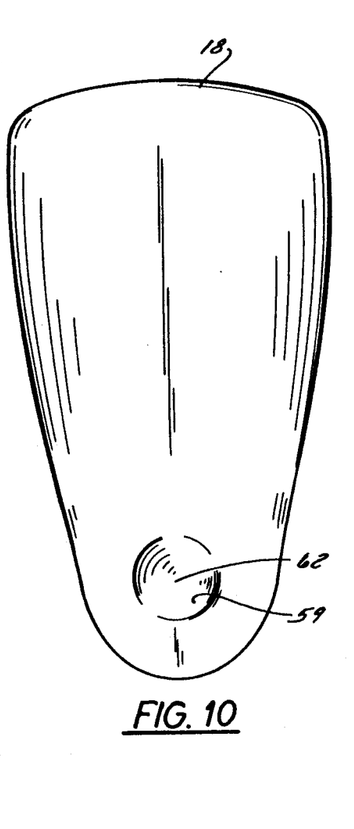
FIG. 10 is a side view showing the inside of one of the exercise pads shown in FIG. 1.

A pair of fluid-filled packs 56, as shown in FIGS. 8 and 9, can also be used in the present invention. The fluid-filled packs 56 have an outer surface made of a material which will stick to the hook fasteners. The two fluid-filled packs are joined by a strap 58 which passes under the foot, and another strap 64 may be used to wrap around the two fluid-filled packs to secure them to the wearer's leg. The fluid-filled packs are chilled by placing them in a freezer, and then they are attached to the inside of the pivot legs 6, 8 by means of the hook connectors on the legs 6, 8 and the mating fabric cover on the packs 56. The fluid-filled packs 56 chill the area of the injury, thereby reducing swelling.

In a typical treatment plan, the chilled packs 56 are applied immediately after injury for about twenty minutes. Then, the cold packs 56 are removed, a compression pad 55 is inserted into the brace on the side of the injury, and an exercise pad 18 or 20 is inserted on the other side. The injured person uses this arrangement of the brace until the swelling goes down. Then the compression pad 55 is removed, and two exercise pads 18, 20 are used.

The arrangement of the present invention permits a single brace 2 to be used through all the stages of treatment and permits the wearer to control the treatment to minimize pain, protect the ankle, reduce swelling, and exercise the ankle as much as possible to promote healing.

Tests have been conducted comparing the present invention using two exercise pads with other ankle supports on the market, and the results were striking. The range of motion for forward and backward flexing (plantarflexion and dorsiflexion) is substantially greater for the present invention than for the Air-Stirrup brand support, the Swedo brand support, or for a taped ankle. The athletes using the present invention were able to apply essentially the same force in plantarflexion as they could without any support, while all other supports reduced the amount of force they could apply. The athletes using the present invention in plantarflexion fatigued at about the same rate as they did without a brace, whereas the users of all other supports exhibited greater fatigue. The present invention also provided substantially greater protection against inversion than all the other supports.

It will be obvious to those skilled in the art that modifications may be made to the embodiments described above without departing from the scope of the present invention.

What is claimed is:

1. An ankle brace to be worn by a wearer to prevent ankle injury or encourage healing of an injured ankle, comprising:
    a heel stirrup, including a bottom portion and inner and outer upright portions;
    inner and outer pivot legs pivotably attached to said inner and outer upright portions at inner and outer pivot points, respectively, wherein the inner pivot point is higher above the bottom portion of the heel stirrup than is the outer pivot point;
    inner and outer exercise pads adopted to lie between the wearer's leg and the inner and outer pivot legs, respectively, said exercise pad defining an indentation adapted to be aligned with the pivot point on its respective pivot leg and extending anterior, posterior, superior, and inferior with respect to the wearer's ankle bone to surround and cup the ankle bone;
    attachment means for releasably attaching the exercise pads to their respective pivot legs and adjusting the exercise pads in either the horizontal or vertical axis; and
    at least one compression pad adapted to replace one of the exercise pads, the compression pad defining an indentation adapted to be aligned with the pivot point on its respective pivot leg and extending anterior, posterior, superior, and inferior with respect to the wearer's ankle bone to surround and cup the ankle bone and being thicker than the exercise pad in the area around the pivot point, wherein the compression pad is adjustable in either the vertical or horizontal axis and releasably attachable to the pivot leg.

2. An ankle brace as recited in claim 1, wherein the compression pad is wider than the exercise pad in the area around the pivot point.

3. An ankle brace as recited in claim 2, wherein the compression pad extends downward from the pivot point farther than does the exercise pad.

4. An ankle brace as recited in claim 1, wherein the compression pad is stiffer than the exercise pad.

5. An ankle brace as recited in claim, and further comprising a pivot strap pivotably connected at one end to the outer upright portion below the outer pivot point, and including pivot strap attachment means for connecting the other end of the pivot strap to the inner pivot leg above the inner pivot point so that the pivot strap lies at an angle to help prevent inversion.

6. An ankle brace as recited in claim 5, wherein the pivot strap is adapted to extend behind the wearer's foot.

7. An ankle brace to be worn by a wearer to prevent ankle injury or encourage healing of an injured ankle, comprising:
   a heel stirrup, including a bottom portion and inner and outer upright portions;
   inner and outer pivot legs pivotably attached to said inner and outer upright portions at inner and outer pivot points, respectively, wherein the outer pivot point is at a lower height relative to the bottom portion than is the inner pivot point; and
   a pivot strap pivotably connected at one end to the outer upright portion below the outer pivot point, and including means for connecting the other end of the pivot strap to the inner pivot leg above the inner pivot point, so that the pivot strap lies at an angle to help prevent inversion.

8. An ankle brace as recited in claim 7, wherein the pivot strap is adapted to extend behind the wearer's foot.

9. An ankle brace as recited in claim 1 further comprising a heel pad adapted to lie on top of the bottom portion of the heel stirrup, said heal pad including a floor panel, having walls on the sides and back so as to cup the wearer's foot to reduce talar tilt.

10. An ankle brace to worn by a wearer to prevent ankle injury or encourage healing of an injured ankle, comprising:
    a heel stirrrup, including a bottom portion and inner and outer upright portions;
    inner and outer pivot legs pivotably attached to said inner and outer upright portions at inner and outer pivot points, respectively;
    inner and outer exercise pads adopted to lie between the wearer's leg and the inner and outer pivot legs, respectively;
    attachment means for adjustably and releasably attaching the exercise pads to their respective pivot legs;
    art least one compression pad adapted to replace one of the exercise pads, the compression pad defining an indentation adapted to be aligned with the pivot point on its respective pivot leg and to cup the wearer's ankle bone and being thicker than the exercise pad in the area around the pivot point, wherein the compression pad is also adjustably and releasably attachable to the pivot leg; and
    a pivot strap pivotably connected at one end to the outer upright portion below the outer pivot point, and including pivot strap attachment means for connecting the other end of the pivot strap to the inner pivot leg above the inner pivot point so that the pivot strap lies at an angle to help prevent inversion.

11. An ankle brace as recited in claim 10, wherein the pivot strap is adapted to extend behind the wearer's foot.

12. An ankle brace as recited in claim 10 further comprising a heel pad adapted to lie on top of the bottom portion of the heel stirrup, said heel pad including a floor panel, having walls on the sides and back so as to cup the wearer's foot to reduce talar tilt.

* * * * *

UNITED STATES PATENT AND TRADEMARK OFFICE
CERTIFICATE OF CORRECTION

PATENT NO. : 5,031,607

DATED : Jul. 16, 1991

INVENTOR(S) : Rick E. Peters

It is certified that error appears in the above-indentified patent and that said Letters Patent is hereby corrected as shown below:

Column 7, line 7, insert the number -- 1,-- after "recited in claim" and before "and further".

Signed and Sealed this

Twelfth Day of April, 1994

Attest:

BRUCE LEHMAN

*Attesting Officer*

*Commissioner of Patents and Trademarks*